(12) United States Patent
Akagane (10) Patent No.: US 11,071,581 B2
(45) Date of Patent: Jul. 27, 2021

(54) TREATMENT INSTRUMENT INCLUDING A RESIN COATING

(71) Applicant: OLYMPUS CORPORATION, Hachioji (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 363 days.

(21) Appl. No.: 16/040,689

(22) Filed: Jul. 20, 2018

(65) Prior Publication Data

US 2018/0325583 A1 Nov. 15, 2018

Related U.S. Application Data

(63) Continuation of application No. PCT/JP2016/051540, filed on Jan. 20, 2016.

(51) Int. Cl.
*A61B 18/00* (2006.01)
*A61B 18/14* (2006.01)
(Continued)

(52) U.S. Cl.
CPC .. *A61B 18/1445* (2013.01); *A61B 17/320092* (2013.01); *A61B 18/00* (2013.01); *A61B 2017/00938* (2013.01); *A61B 2017/320094* (2017.08); *A61B 2018/0013* (2013.01); *A61B 2018/00077* (2013.01); *A61B 2018/00083* (2013.01); *A61B 2018/00101* (2013.01);
(Continued)

(58) Field of Classification Search
CPC ............ A61B 18/1445; A61B 18/00; A61B 17/320092; A61B 2018/0013; A61B 2018/00142; A61B 2017/320094; A61B 2017/00938; A61B 2018/00077; A61B 2018/00083; A61B 2018/00101; A61B 2018/00994; A61B 2018/1457
USPC .......................................................... 606/27
See application file for complete search history.

(56) References Cited

U.S. PATENT DOCUMENTS 4,500,647 A * 2/1985 Solomon ................. C25B 11/00
156/308.2
5,100,402 A 3/1992 Fan
(Continued)

FOREIGN PATENT DOCUMENTS

CN 101883530 A 11/2010
EP 0479482 A1 4/1992
(Continued)

OTHER PUBLICATIONS

Jun. 11, 2019 Office Action issued in Japanese Patent Application No. 2017-562210.
(Continued)

*Primary Examiner* — Linda C Dvorak
*Assistant Examiner* — Nils A Potter
(74) *Attorney, Agent, or Firm* — Oliff PLC (57) ABSTRACT

A treatment instrument includes a treatment section treating a target of treatment such as a living tissue. The treatment section has an outer surface. A first resin film (first resin coating) covers part of the outer surface of the treatment section. A second resin film (second resin coating) covers at least a boundary between a region covered by the first resin film and a region not covered by the first resin film on the outer surface of the treatment section.

8 Claims, 6 Drawing Sheets

(51) Int. Cl.
*A61B 17/32* (2006.01)
*A61B 17/00* (2006.01)
(52) U.S. Cl.
CPC ............ *A61B 2018/00142* (2013.01); *A61B 2018/00994* (2013.01); *A61B 2018/1457* (2013.01)

(56) References Cited

U.S. PATENT DOCUMENTS

| | | | | |
|---|---|---|---|---|
| 5,308,311 | A * | 5/1994 | Eggers | A61B 17/3211 600/28 |
| 10,045,794 | B2 * | 8/2018 | Witt | A61B 17/320092 |
| 2001/0031964 | A1 | 10/2001 | Gentelia et al. | |
| 2003/0109876 | A1 | 6/2003 | Yamauchi | |
| 2003/0199870 | A1 * | 10/2003 | Truckai | A61B 18/1442 606/51 |
| 2007/0154760 | A1 * | 7/2007 | Zhu | H01M 8/0618 429/494 |
| 2009/0143806 | A1 * | 6/2009 | Witt | A61L 31/10 606/169 |
| 2012/0222890 | A1 * | 9/2012 | Yoshida | H05K 3/1283 174/255 |
| 2013/0274736 | A1 * | 10/2013 | Garrison | A61B 18/1445 606/41 |
| 2016/0144204 | A1 | 5/2016 | Akagane | |
| 2016/0175000 | A1 | 6/2016 | Akagane | |

FOREIGN PATENT DOCUMENTS

| | | |
|---|---|---|
| JP | H06-339485 A | 12/1994 |
| JP | H07-509620 A | 10/1995 |
| JP | 2003-175054 A | 6/2003 |
| JP | 2003-524500 A | 8/2003 |
| JP | 2011-505198 A | 2/2011 |
| WO | 2009/073402 A2 | 6/2009 |
| WO | 2015/020147 A1 | 2/2015 |
| WO | 2015/118757 A1 | 8/2015 |
| WO | 2015/178270 A1 | 11/2015 |

OTHER PUBLICATIONS

Jul. 24, 2018 International Preliminary Report on Patentability issued in International Patent Application No. PCT/JP2016/051540.
May 29, 2020 Office Action issued in Chinese Patent Application No. 201680079548.7.
Aug. 28, 2019 Extended European Search Report issued in European Patent Application No. 16886292.8.
Apr. 19, 2016 International Search Report issued in International Patent Application No. PCT/JP2016/051540.

* cited by examiner

TREATMENT INSTRUMENT INCLUDING A RESIN COATING

CROSS-REFERENCE TO RELATED APPLICATIONS

This is a Continuation Application of PCT Application No. PCT/JP2016/051540, filed Jan. 20, 2016, the entire contents of which are incorporated herein by reference.

BACKGROUND OF THE INVENTION

1. Field of the Invention

The present invention relates to a treatment instrument for treating a target of treatment such as a living tissue.

2. Description of the Related Art

International Publication No. 2009/073402 discloses a treatment instrument for treating a target of treatment (a living tissue) grasped between a treatment section and a grappling member, by using ultrasonic vibration transmitted to the treatment section. At least part of the outer surface of the treatment section of this treatment instrument is covered by a coating (resin film).

BRIEF SUMMARY OF THE INVENTION

According to one aspect of the invention, a treatment instrument includes that: a treatment section having an outer surface, the treatment section configured to treat a target of treatment; a first resin film covering part of the outer surface of the treatment section; and a second resin film covering at least a boundary between a region covered by the first resin film and a region not covered by the first resin film on the outer surface of the treatment section, wherein the outer surface includes a treatment surface configured to treat the target of treatment, the first resin film has a higher electric resistance and a thermal resistance, at least one of which is higher than that of the treatment section, and the first resin film is located on the outer surface of the treatment section in a position away from the treatment surface.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
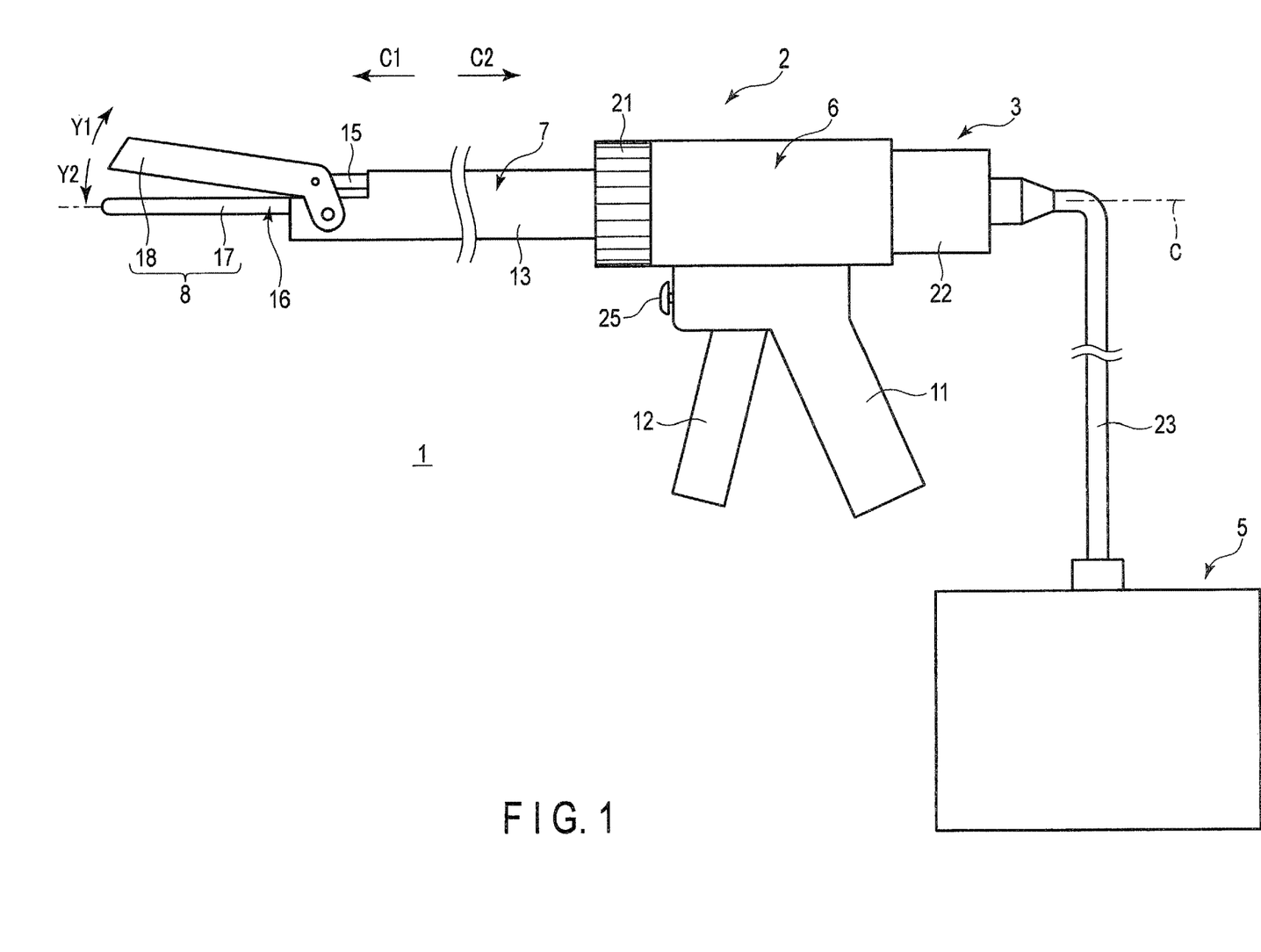
FIG. 1 is a schematic diagram showing a treatment system according to a first embodiment.

The first embodiment of the present invention will be described with reference to FIGS. 1-4. FIG. 1 is a diagram showing a treatment system 1 according to the present embodiment. As shown in FIG. 1, the treatment system 1 includes a treatment instrument (hand piece) 2, a transducer unit 3, and an energy control device 5. The treatment instrument 2 has a longitudinal axis C. Here, the direction along the longitudinal axis C is defined as the longitudinal direction (the direction indicated by the arrows C1 and C2). One side in the longitudinal direction is the distal side (arrow C1 side), and the side opposite to the distal side is the proximal side (arrow C2 side).

The treatment instrument 2 includes a housing 6 that can be held, a shaft portion (shaft) 7 that is connected to the housing 6 from the distal side, and an end effector 8 that is provided in the distal part of the shaft portion 7. The housing 6 includes a grip (fixed handle) 11 extending along a direction crossing the longitudinal axis C. A handle (movable handle) 12 is rotatably attached to the housing 6. As the handle 12 rotates with respect to the housing 6, the handle 12 opens or closes with respect to the grip 11.

The shaft portion 7 includes a cylindrical sheath 13 forming the exterior, and a movable portion (movable member) 15 extending inside the sheath 13. Each of the sheath 13 and the movable portion 15 extends along the longitudinal axis C (in the longitudinal direction). Inside the housing 6, the handle 12 is connected to the proximal portion of the movable portion 15. By opening or closing the handle 12 with respect to the grip 11, the movable part 15 moves in the longitudinal direction (along the longitudinal axis C) with respect to the housing 6 and the sheath 13.

From the inside of the housing 6, a rod member (probe) 16 extends toward the distal side. In the present embodiment, the rod member 16 is made of a conductive material having a high vibration transmissibility, and is formed of, for example, Ti-6Al-4V, titanium alloy, duralumin or the like. The rod member 16 is inserted through the shaft portion 7, and extends along the longitudinal axis C through the inside of the shaft portion 7 (sheath 13 and movable portion 15). A treatment section (probe treatment section) 17 is formed in the distal part of the rod member 16. The treatment section (first gripping piece) 17 protrudes from the distal end of the shaft portion 7 towards the distal side. In a part of the rod member 16 which is located on the proximal side with respect to the treatment section 17 (that is, in the portion extending inside of the shaft portion 7), the central axis is substantially coaxial with the longitudinal axis C.

A grasping member (jaw) 18 is rotatably attached to the distal part of the sheath 13. The distal part of the movable portion (movable pipe) 15 is connected to the grasping member (second gripping piece) 18. As the movable portion 15 moves along the longitudinal axis C in response to movement of the handle 12, the grasping member 18 is rotated and the space between the treatment section 17 and the grasping member 18 opens or closes. In the present embodiment, the end effector 8 is formed by the treatment section 17 and the grasping member 18. As the space between the treatment section 17 and the grasping member 18 closes, it becomes possible to grip a target of treatment such as a living tissue between the treatment section 17 and the grasping member 18. The opening and closing direction (direction indicated by the arrows Y1 and Y2) between the treatment section 17 and the grasping member 18 intersects (is substantially perpendicular to) the longitudinal axis C (longitudinal direction).

A rotary knob 21 is attached to the housing 6, and the rotary knob 21 is fixed to the sheath 13. By rotating the rotary knob 21 about the longitudinal axis C relative to the housing 6, the shaft portion 7, the end effector 8 and the rod member (vibration transmitting member) 16 rotate together around the longitudinal axis C with respect to the housing 6.

The transducer unit 3 is connected to the housing 6 from the proximal side. The transducer unit 3 includes a transducer case 22 and an ultrasonic transducer (not shown) provided inside the transducer case 22. Inside the housing 6, the transducer case 22 is attached to the shaft portion 7 from the proximal side. Inside the housing 6, the rod member 16 is connected to the distal side of the ultrasonic transducer.

One end of a cable 23 is connected to the transducer unit 3, and the other end of the cable 23 is detachably connected to the energy control device 5. The energy control device 5 includes an electric power source such as a battery or an outlet, a conversion circuit, a processor or an integrated circuit and the like including a CPU (Central Processing Unit) or an ASIC (application specific integrated circuit) and the like, and a storage medium. An operation button 25 as an energy operation section is attached to the housing 6.

When an operation input is performed by the operation button 25 in the treatment system 1, a first energy (vibration-generating electric energy) is supplied from the energy control device 5 to the ultrasonic transducer. In this manner, ultrasonic vibration is generated by the ultrasonic transducer, and the generated ultrasonic vibration is transmitted from the proximal side to the distal side in the rod member 16. By transmitting ultrasonic vibration, the rod member 16 including the treatment section 17 resonates. The treatment section 17 then treats the target of treatment grasped between the treatment section 17 and the grasping member 18 by using the transmitted ultrasonic vibration.

When the operation input is performed by the operation button 25, a second electric energy (high-frequency electric energy) different from the first electric energy is supplied from the energy control device 5 to the treatment section 17 and the grasping member 18. The treatment section 17 and the grasping member 18 thus function as electrodes having different potentials with respect to each other. In this manner, high-frequency current flows to the target of treatment grappled between the treatment section 17 and the grasping member 18, high-frequency current used to treat the target of treatment.

Figure 2:
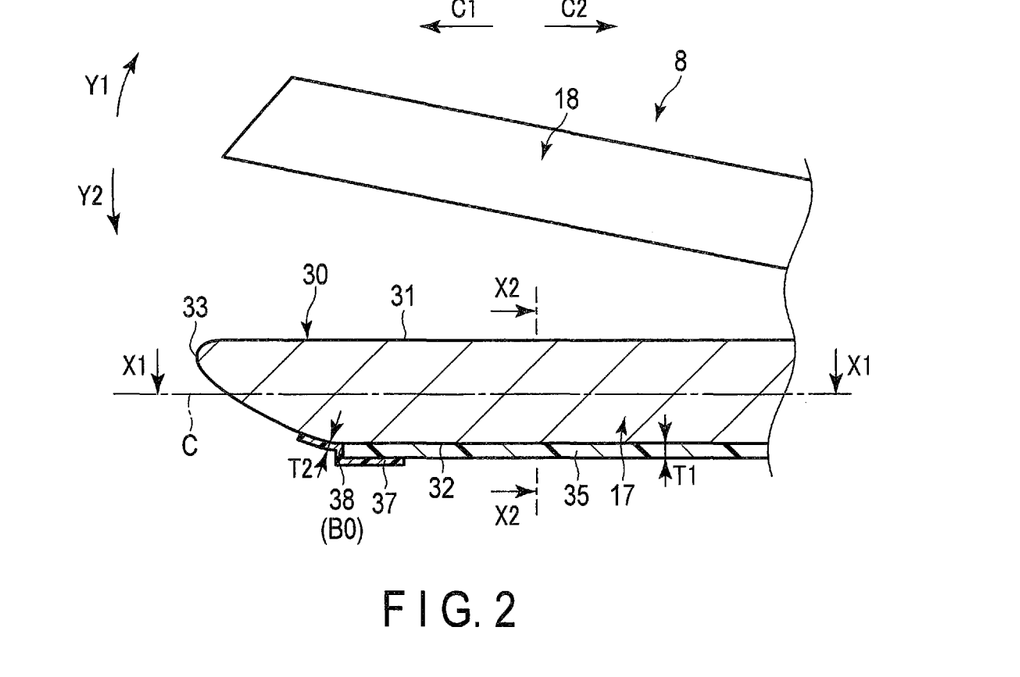
FIG. 2 is a schematic diagram showing an end effector according to the first embodiment.
Figure 3:
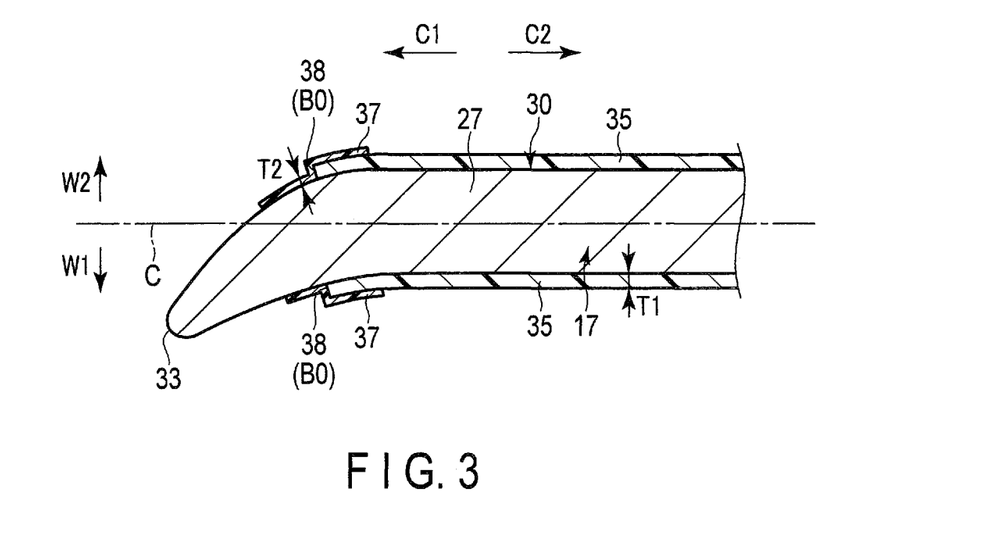
FIG. 3 is a cross-sectional view along the line X1-X1 shown in FIG. 2.
Figure 4:
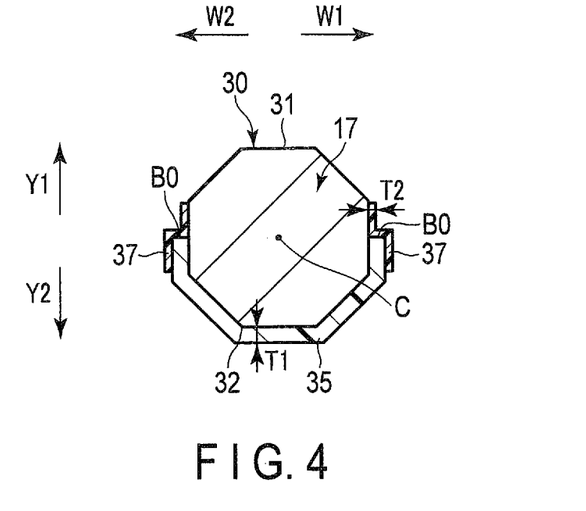
FIG. 4 is a cross-sectional view along the line X2-X2 shown in FIG. 2.

FIG. 2 shows the configuration of the end effector 8. FIG. 3 shows the X1-X1 section of FIG. 2, and FIG. 4 shows the X2-X2 section of FIG. 2. Here, the direction, which is intersecting with (substantially perpendicular to) the longitudinal axis C (longitudinal direction) and intersecting with (substantially perpendicular to) the opening and closing direction of the end effector 8 (direction indicated by the arrows Y1 and Y2), is defined as the width direction of the end effector 8 (direction indicated by the arrow W1 and the arrow W2). In FIG. 2, the treatment section 17 is shown by a cross section substantially perpendicular to the width direction of the end effector 8. In FIG. 3, the treatment section 17 is shown in across section substantially perpendicular to the opening and closing direction of the end effector 8, and in FIG. 4, the treatment section 17 is shown by a cross section substantially perpendicular to the longitudinal axis C.

As shown in FIGS. 2 to 4, in the present embodiment, the treatment section 17 includes a curved extension 27 curving away from the longitudinal axis C to one side in the width direction of the end effector 8 (arrow W1 side). The curved extension 27 is provided in the distal part of the treatment section 17. The treatment section 17 has an outer surface (outer surface of the treatment section) 30. The outer surface 30 includes an opposing surface 31 opposing to the grasping member 18, and a back surface 32 facing a side opposite to the opposing surface 31 in the opening and closing direction of the end effector 8. The outer surface 30 has a distal surface 33 that forms the distal end of the treatment section 17 (tip of the rod member 16).

Part of the outer surface 30 of the treatment section 17 is covered by a first resin film (first resin coating) 35. However, in the present embodiment, the first resin film 35 does not cover the opposing surface 31 and the distal surface 33. In other words, the first resin film 35 covers at least part (for example, the back surface 32) of the region other than the opposing surface 31 and the distal surface 33, and is located in a position away from the opposing surface 31 and the distal surface 33 on the outer surface 30 of the treatment section 17. In the present embodiment, the coating process onto the outer surface 30 of the first resin film 35 is realized by, for example, applying the material for forming the first resin film 35 onto part of the outer surface 30 of the treatment section 17.

The first resin film 35 is made of, for example, PEEK (polyether ether ketone), and it is electrically insulating. Therefore, the first resin film 35 has a higher electric resistance than the conductive treatment section 17 (rod member 16). The first resin film 35 also has a higher thermal resistance than the treatment section 17 (rod member 16) which is formed of a metal such as Ti-6Al-4V. The first resin film 35 thus has a lower thermal conductivity than the treatment section 17. The first resin film 35 has a film thickness (first film thickness) T1. In one example, the film thickness T1 is greater than or equal to 40 microns and less than or equal to 60 microns, and is approx. 50 microns.

Part of the outer surface 30 of the treatment section 17 is covered by a second resin film (second resin coating) 37 formed of a material different from the material of the first resin film 35. The second resin film 37 in the present embodiment covers the outer surface 30 of the treatment section 17 at only the boundary B0 between the region covered by the first resin film 35 and the region not covered by the first resin film 35 and its vicinity. The second resin film 37 thus covers at least the boundary B0 between the region covered by the first resin film 35 and the region not covered by the first resin film 35. In the present embodiment, the coating process of the second resin film 37 onto the outer surface 30 and onto the first resin film 35 is realized by, for example, applying the material for forming the second resin film 37 onto part of the outer surface 30 of the treatment section 17 and onto part of the first resin film 35. By applying the second resin film 37 onto the region covered by the first resin film 35 on the outer surface 30 of the treatment section 17, the second resin film 37 is laminated onto the outer side of the first resin film 35, thereby forming a two-layer structure.

The second resin film 37 is formed of a fluorine resin having C—F bonds (carbon-fluorine bonds), such as PTFE (polytetrafluoroethylene) or PFA (perfluoroalkoxy alkane). The second resin film 37 is thus water and oil repellent. The second resin film 37 also has a film thickness (second film thickness) T2. The film thickness T2 of the second resin film 37 is smaller than the film thickness T1 of the first resin film 35. In one example, the film thickness T2 of the second resin film 37 is 1 micron or less, and is approx. 0.1 micron. The thickness T2 of the second resin film 37 is then 1/50 or less of the film thickness T1 of the first resin film 35.

The first resin film 35 has a distal boundary 38 as part of the boundary B0. The distal boundary 38 forms the distal end of the first resin film 35, and is located in the distal part of the treatment section 17. As mentioned above, the second resin film 37 covers at least the boundary B0. Thus, the second resin film 37 covers the distal boundary 38 and its vicinity, within a range across the distal boundary 38. In other words, with the interposed distal boundary 38, the second resin film 37 covers both the proximal side and the distal side of distal boundary 38.

Next, the functions and effects of the treatment instrument 2 according to the present embodiment will be described. For treatment using the treatment instrument 2, the end effector 8 is first inserted into the body cavity such as the abdominal cavity. The target of treatment such as a living tissue (blood vessel) is then positioned between the treatment section 17 and the grasping member 18, and by operating the handle 12, the space between the treatment section 17 and the grasping member 18 is closed. In this manner, the target of treatment is grasped between the treatment section 17 and the grasping member 18. By then the operation input in the operation button 25 as the energy operation section, the gripped target of treatment is treated by using ultrasonic vibration and high-frequency current, as mentioned above.

In the present embodiment, the first resin film 35 does not cover the opposing surface 31 facing the grasping member 18. In this manner, high-frequency current thus appropriately flows through the target of treatment between the opposing surface 31 of the treatment section 17 and the grasping member 18, thereby ensuring the performance of the treatment using high-frequency current.

At least part of the portion other than the opposing surface 31 and the distal surface 33 of the outer surface 30 of the treatment section 17 is covered by the highly electrically resistant first resin film 35. Therefore, release of high-frequency electric energy from the treatment section 17 through the first resin film 35 is effectively prevented, even when the region covered by the first resin film 35 comes into contact with a living tissue other than the target of treatment. In this manner, high-frequency electric energy is effectively prevented from being released from a region other than the opposing surface 31 on the outer surface 30 of the treatment section 17, thereby increasing the density of high-frequency current flowing to the target of treatment between the treatment section 17 and grasping member 18. By increasing the current density of high-frequency current flowing through the target of treatment, the performance of treatment per high-frequency current is improved.

Treatments using energies such as ultrasonic vibration and high-frequency current generate heat. For this reason, the treatment section 17 heats up to a high temperature during the time of treatment. In the present embodiment, at least part of the region on the outer surface 30 of the treatment section 17 other than the opposing surface 31 and the distal surface 33 is covered by the first resin film 35 having high thermal resistance. Therefore, thermal damage of the living tissue is effectively prevented, even when the region covered by the first resin film 35 comes into contact with the living tissue or the like other than the target of treatment.

As the treatment section 17 resonates by ultrasonic vibration, the rod member 16 including the treatment section 17 vibrates longitudinally substantially in parallel with the longitudinal axis C. If liquids such as water then exist in the distal surface 33 or its vicinity, cavitation occurs in the distal surface 33 and its vicinity. In the present embodiment, the distal surface 33 is not covered by the first resin film 35. In this manner, the first resin film 35 is effectively prevented from peeling off the outer surface 30 of the treatment section 17 by cavitation.

During the treatment, the treatment section 17 may be caused to vibrate by ultrasonic vibration while the treatment section 17 is immersed in a liquid such as water or blood, or the treatment section 17 may be heated to a high temperature by the treatment energy. In the present embodiment, the second resin film 37 is coated at least in the boundary B0 between the region covered by the first resin film 35 and the region not covered by the first resin film 35. In this manner, even when the treatment section 17 is immersed in a liquid, the liquid is prevented from entering into the inner side of the first resin film 35 (between the outer surface 30 of the treatment section 17 and the first resin film 35) at the boundary B0, so that the first resin film 35 is effectively prevented from peeling off the outer surface 30 of the treatment section 17.

The second resin film 37 covering at least the boundary B0 is formed of a fluorine resin and has water and oil repellent. Liquids (water, oil, etc.) are thus effectively prevented from entering into the inner side of the first resin film 35 at the boundary B0, so that the first resin film 35 is additionally effectively prevented from peeling off the outer surface 30 of the treatment section 17.

While the treatment section 17 is caused to vibrate by ultrasonic vibration, the distal end of the treatment section becomes the antinode of vibration (longitudinal vibration), so that the amplitude and vibration speed are large in the distal portion of the treatment section 17 where the distal boundary 38 of the first resin film 35 is located. In the present embodiment, the distal boundary 38 is part of the boundary B0, and the range across the distal boundary 38 is covered by the second resin film 37. In this manner, even in the distal part of the treatment section 17 where the amplitude and vibration speed are increased, liquids from the distal boundary 38 (boundary B0) are effectively prevented from entering into the inner side of the first resin film 35, so that the first resin film 35 is effectively prevented from peeling off the outer surface 30 of the treatment section 17.

(Modifications)

Figure 5:
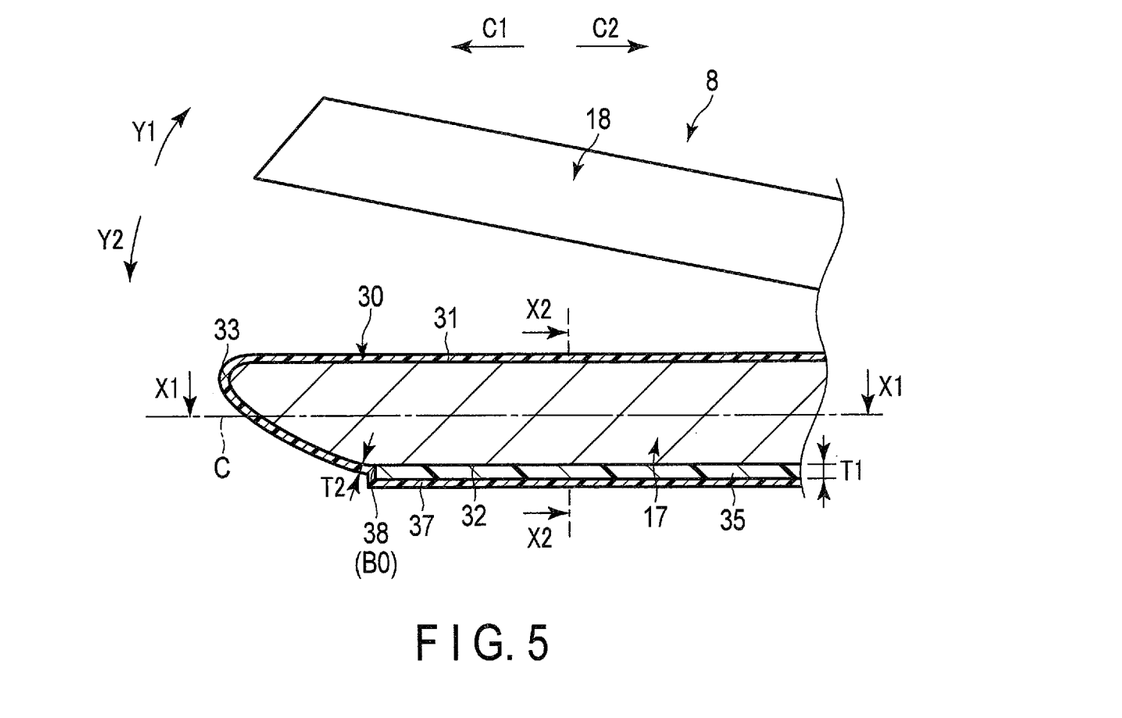
FIG. 5 is a schematic diagram showing an end effector according to a first modification.
Figure 6:
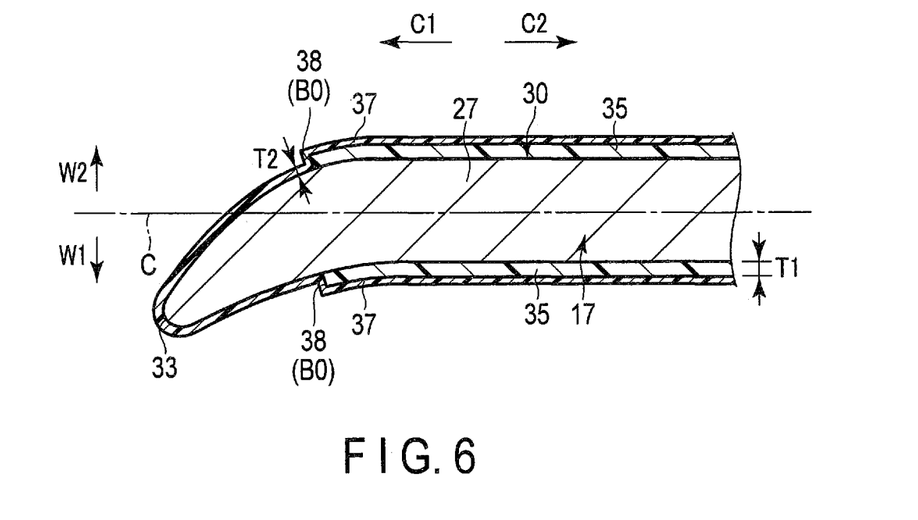
FIG. 6 is a cross-sectional view along the line X1-X1 shown in FIG. 5.
Figure 7:
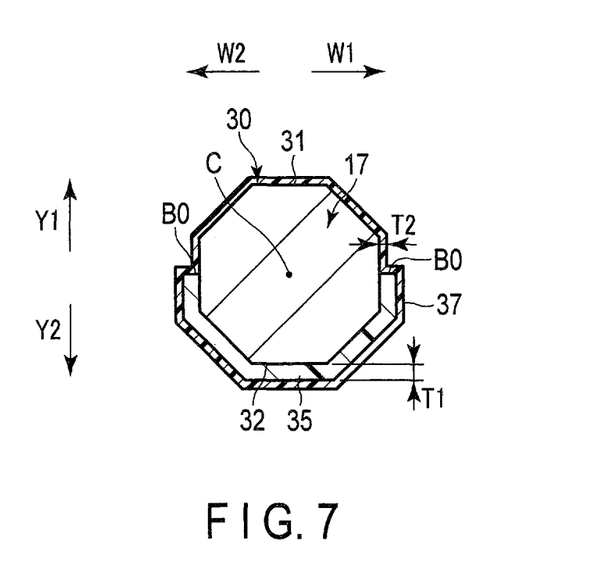
FIG. 7 is a cross-sectional view along the line X2-X2 shown in FIG. 5.

In the first embodiment, the second resin film 37 only covers the boundary B0 between the region covered by the first resin film 35 and the region not covered by the first resin film 35 and its vicinity on the outer surface 30 of the treatment section 17; however, the embodiments are not limited to this. For example, as shown in FIGS. 5-7 as a first modification, the second resin film 37 may cover the entire outer surface 30 of the treatment section 17. In the present modification, likewise, the second resin film 37 covers the boundary B0 between the region covered by the first resin film 35 and the region not covered by the first resin film 35 on the outer surface 30 of the treatment section 17. In this manner, it is possible to prevent, similar to the first embodiment, liquids from entering into the inner side of the first resin film 35 (between the outer surface 30 of the treatment section 17 and the first resin film 35) at the boundary B0, and thus effectively prevent the first resin film 35 from peeling off the outer surface 30 of the treatment section 17.

In FIG. 5, the treatment section 17 is shown by a cross section substantially perpendicular to the width direction of the end effector 8. FIG. 6 shows a cross section taken along the line X1-X1 shown in FIG. 5, and shows the treatment section 17 in a cross section substantially perpendicular to the opening and closing direction of the end effector 8. FIG. 7 shows a cross section taken along the line X2-X2 shown in FIG. 5, and the treatment section 17 is shown in a cross section substantially perpendicular to the longitudinal axis C.

In the present embodiment, for example, the process of coating of the second resin film 37 onto the outer surface 30 and the first resin film 35 is carried out by, for example, dipping the treatment section 17 in a solvent or the like of the material for forming the second resin film 37. In this manner, the coating process is carried out more easily than when applying the material for forming the second resin film 37.

The film thickness T2 of the second resin film 37 is thin and 1 μm or less. In other words, the film thickness T2 of the second resin film 37 is ⅟50 or less of the film thickness T1 of the first resin film 35. Thus, high-frequency current appropriately flows between the opposing surface 31 of the treatment section 17 and the grasping member 18 through the target of treatment (and the second resin film 37) even when the second resin film 37 covers the opposing surface 31 facing the grasping member 18.

Also, in the present modification, the lubricity of the opposing surface 31 is increased, since the second resin film 37 which is formed of a fluorine resin covers the opposing surface 31. Therefore, adhesion to the opposing surface 31 of the target of treatment gripped between the opposing surface 31 of the treatment section 17 and the grasping member 18 is effectively prevented.

In the previously-mentioned embodiment, the handle 12 is located, for example, on the distal side with respect to the grip 11, and moves substantially in parallel with the longitudinal direction during opening or closing motion; however, the embodiments are not limited to this. In a modification, the handle 12 may, for example, be located proximally with respect to the grip 11, and in another modification, the handle 12 may, during opening or closing motion, move in the direction transverse to the longitudinal direction. In yet another modification, the rotary knob 21 may not be provided.

Figure 8:
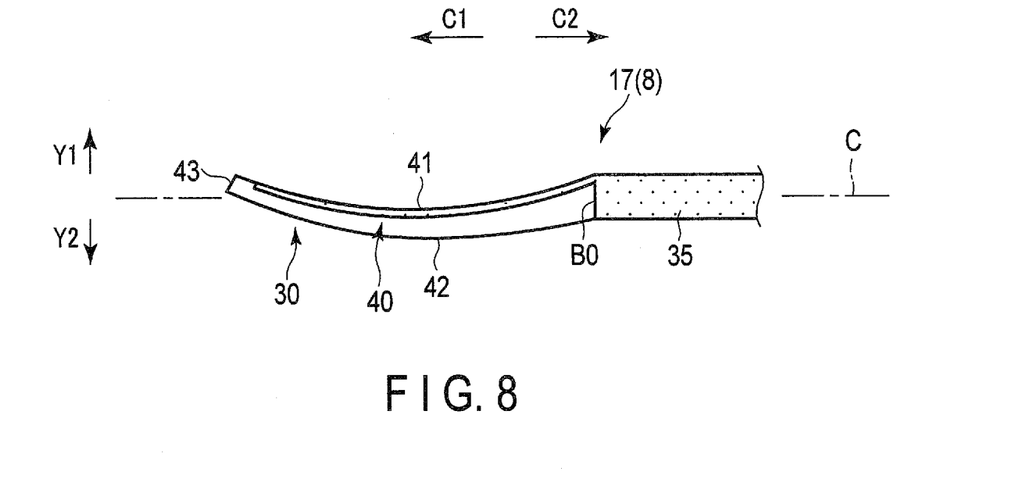
FIG. 8 is a schematic view of a treatment section according to a second modification as viewed from one side in the width direction.
Figure 9:
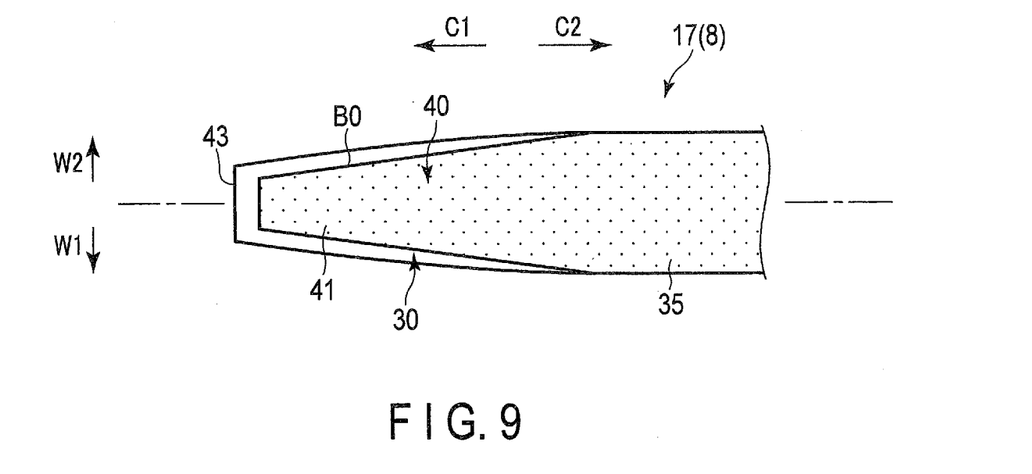
FIG. 9 is a schematic view of the treatment section according to the second modification as viewed from a first curved surface side.

In the previously-mentioned embodiment, the end effector 8 is provided with the grappling member 18; however, the embodiments are not limited to this. For example, as shown in FIGS. 8-9 as a second modification, the grasping member 18 may not be provided and the end effector 8 may be formed only from the treatment section (probe treatment section) 17. In the present modification, the treatment section 17 includes a spatula-shaped portion 40, and the distal end of the treatment section 17 (tip of the rod member 16) is formed by the spatula-shaped portion 40. In the spatula-shaped portion 40, the dimension in the width direction of the treatment section 17 (the direction indicated by the arrows W1 and W2) is larger than the dimension in the thickness direction of the treatment section 17 (the direction indicated by the arrows Y1 and Y2).

The outer surface 30 of the treatment section 17 has a first curved surface 41 facing one side (arrow Y1 side) in the thickness direction in the spatula-shaped portion 40, and a second curved surface 42 facing the side opposite to the first curved surface 41 in the spatula portion 40. As viewed from one side in the width direction (for example, arrow W1 side), each of both the first curved surface 41 and the second curved surface 42 is formed in a substantially arc-shape, each substantially arc-shape having its center located on one side in the thickness direction (arrow Y1 side) with respect to the longitudinal axis C. The outer surface 30 of the treatment section 17 is provided with a distal surface 43 forming the distal end of the treatment section 17 (the tip of the spatula-shaped portion 40).

In the present modification, likewise, part of the outer surface 30 of the treatment section 17 is covered by the first resin film (first resin coating) 35. In the present modification, the second curved surface 42 and the distal surface 43 are not covered by the first resin film 35. In other words, the first resin film 35 covers at least part (for example, the first curved surface 41) of the portion other than the second curved surface 42 and the distal surface 43 on the outer surface 30 of the treatment section 17. In the present modification, likewise, the first resin film 35 is formed of material having highly electrically resistant and highly thermally resistant such as PEEK. FIG. 8 is a view of the treatment section 17 as viewed from one side in the width direction (arrow W1 side), and FIG. 9 is a view of the treatment section 17 as viewed from the side of the first curved surface 41. In FIGS. 8 and 9, the region covered by the first resin film 35 is indicated by the dotted hatching.

In the present modification, the target of treatment is abraded by the treatment section 17 (rod member 16) vibrating per ultrasonic vibration while the distal part of the first curved surface 41 is in contact with the target of treatment. By supplying high-frequency electrical energy to the treatment section 17 while the second curved surface 42 is in contact with the target of treatment, high-frequency current flows through the target of treatment between the second curved surface 42 and the counter electrode plate (not shown) provided outside the body. As mentioned above, in the present modification, likewise, the target of treatment is treated using a treatment energy such as ultrasonic vibration and high-frequency current.

In the present modification, likewise, on the outer surface 30 of the treatment section 17, the second resin film 37 covers at least the boundary B0 between the region covered by the first resin film 35 (region indicated by the dotted hatching) and the region not covered by the first resin film 35 (region without hatching). Therefore, similarly to the previously-mentioned embodiment, liquids are prevented at the boundary B0 from entering into the inner side of the first resin film 35 (between the outer surface 30 of the treatment section 17 and the first resin film 35), so that the first resin film 35 is effectively prevented from peeling off the outer surface 30 of the treatment section 17.

Figure 10:
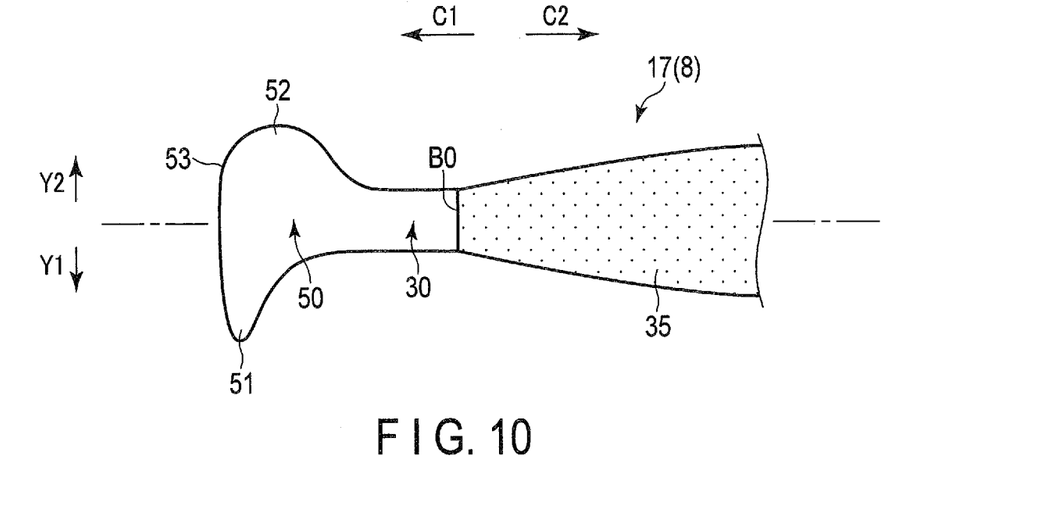
FIG. 10 is a schematic diagram showing a treatment section according to a third modification.

As a third modification, as shown in FIG. 10, instead of the spatula-shaped portion 40, a hook-like portion 50 may be provided in the treatment section 17. In the present modification, the distal end of the treatment section 17 (tip of the rod member 16) is formed by the hook-like portion 50. FIG. 10 is a view of the treatment section 17 as viewed from one side in the width direction; in FIG. 10, the direction perpendicular to the plane of the paper substantially coincides with the width direction of the treatment section 17.

Here, a direction, which is intersecting with (substantially perpendicular to) the longitudinal axis C (longitudinal direction) and intersecting with (substantially perpendicular to) the width direction of the treatment section 17, is referred to as the intersecting direction (the direction indicated by the arrows Y1 and Y2). The hook-like portion 50 includes a first protrusion 51 protruding to one side in the intersecting direction (arrow Y1 side), and a second protrusion 52 protruding to the opposite side of the first protrusion 51. The outer surface 30 of the treatment section 17 is provided with a distal surface 53 that forms the distal end of the treatment section 17 (the tip of the hook-like portion 50).

In the present modification, the target of treatment is grappled by the first protrusion 51, and the treatment section 17 (rod member 16) is caused to vibrate by ultrasonic vibration, whereby the target of treatment is abraded. By then supplying high-frequency electric energy to the treatment section 17, high-frequency current may flow through the treatment object between the hook-like portion 50 and the counter electrode plate (not shown) arranged outside the body. As mentioned above, in the present modification, likewise, the target of treatment is treated per treatment energy such as ultrasonic vibration.

In the present modification, likewise, part of the outer surface 30 of the treatment section 17 is covered by the first resin film (first resin coating) 35. In the present modification, the first resin film 35 does not cover the hook-like portion 50. In other words, the first resin film 35 is covered by at least part of the section other than the hook-like portion 50 on the outer surface 30 of the treatment section 17. In FIG. 10, the region covered by the first resin film 35 is indicated by the dotted hatching.

In the present modification, likewise, on the outer surface 30 of the treatment section 17, the second resin film 37 covers at least the boundary B0 between the region covered by the first resin film 35 (region indicated by the dotted hatching) and the region not covered by the first resin film 35 (region without hatching). In this manner, similarly to the previously-mentioned embodiment, liquids are prevented at the boundary B0 from entering into the inner side of the first resin film 35 (between the outer surface 30 of the treatment section 17 and the first resin film 35), so that the first resin film 35 is effectively prevented from peeling off the outer surface 30 of the treatment section 17.

Figure 11:
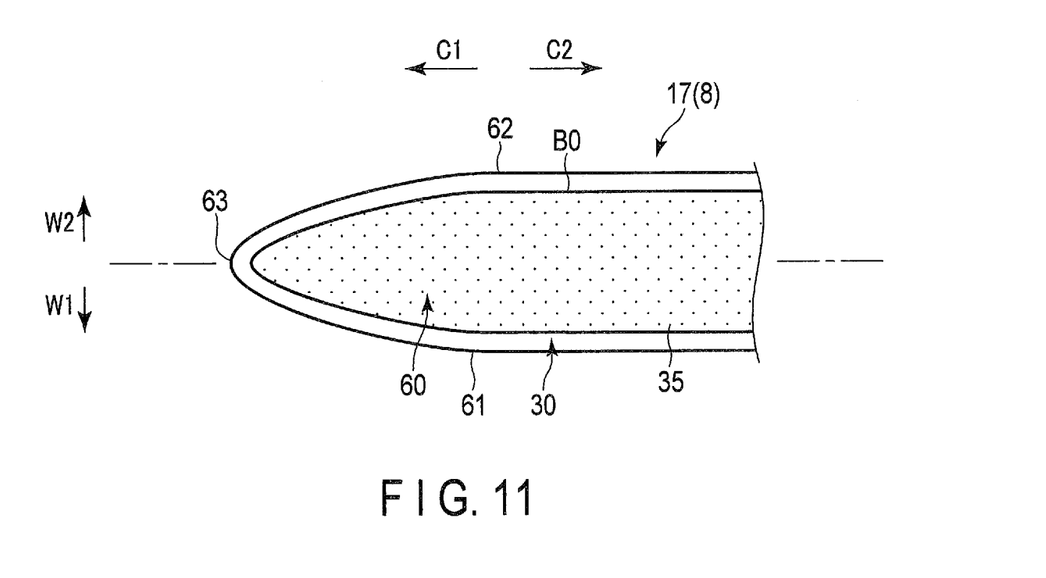
FIG. 11 is a schematic diagram showing a treatment section according to a fourth modification.

As a fourth modification, as shown in FIG. 11, instead of the spatula-shaped portion 40, a blade-forming portion 60 may be provided in the treatment section 17. In the present modification, the distal end of the treatment section 17 (tip of the rod member 16) is formed by the blade-forming portion 60. FIG. 11 is a view of the treatment section 17 as viewed from one side in the thickness direction, and in FIG. 11, the direction perpendicular to the plane of the paper substantially coincides with the thickness direction of the treatment section 17.

Here, the direction, which is intersecting with (substantially perpendicular to) the longitudinal axis C (longitudinal direction) and intersecting with (substantially perpendicular to) the thickness direction of the treatment section 17, is referred to as the width direction (direction indicated by the arrows W1 and W2). The blade-forming portion 60 is provided with a first side cutting edge 61 formed at the edge on one side in the width direction (arrow W1 side), and with a second side cutting edge 62 formed at the edge opposite to the first side cutting edge 61. The blade-forming portion 60 of the treatment section 17 is provided with a distal blade 63 forming the distal end of the treatment section 17 (tip of the blade-forming portion 60).

In the present modification, while at least one of the side blades 61, 62 and the distal blade 63 is in contact with the target of treatment, the treatment section 17 (rod member 16) is caused by ultrasonic vibration to vibrate and high-frequency electrical energy is supplied to the treatment section 17. In this manner, the target of treatment is abraded. At this point, high-frequency current flows through the target of treatment between the blade-forming portion 60 and the counter electrode plate (not shown) provided outside the body. As mentioned above, in the present modification, likewise, the target of treatment is treated by treatment energy such as ultrasonic vibration and high-frequency current.

In the present modification, likewise, part of the outer surface 30 of the treatment section 17 is covered by the first resin film (first resin coating) 35. In the present modification, the first resin film 35 does not cover the side blades 61, 62 and the leading edge blade 63. In other words, the first resin film 35 covers at least part of the portion other than the side blades 61, 62 and the distal blade 63 on the outer surface 30 of the treatment section 17. In FIG. 11, the region covered by the first resin film 35 is indicated by the dotted hatching.

In the present modification, likewise, the second resin film 37 covers at least the boundary B0 between the region covered by the first resin film 35 (region indicated by the dotted hatching) and the region not covered by the first resin film 35 (region without hatching) on the outer surface 30 of the treatment section 17. In this manner, similarly to the previously-mentioned embodiment, liquids are prevented at the boundary B0 from entering into the inner side of the first resin film 35 (between the outer surface 30 of the treatment section 17 and the first resin film 35), so that the first resin film 35 is effectively prevented from peeling off the outer surface 30 of the treatment section 17.

In the previously-mentioned embodiment, at least one of ultrasonic vibration and high-frequency current is used as treatment energy; however, the embodiments are not limited to this. For example, the heat generated by the heat generating body provided in the end effector (8) may be used as the treatment energy. In this case, the transducer unit 3 is not provided in the treatment system 1, and heat-generated electric energy is supplied from the energy control device 5 to the heat generating body.

In the previously-mentioned embodiment, the treatment instrument (2) includes the treatment section (17) configured to treat the target of treatment, and the treatment section (17) includes the outer surface (30). Part of the outer surface (30) of the treatment section (17) is covered by the first resin film (35). On the outer surface (30) of the treatment section (17), the second resin film (37) covers at least the boundary (B0) between the region covered by the first resin film (35) and the region not covered by the first resin film (35). Such configuration can be applied appropriately, irrespective of the configuration of the treatment section (17) (configuration of the end effector (8)) and the type of treatment energy.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument comprising:
a treatment section having an outer surface, the treatment section configured to treat a target of treatment;
a first resin film covering part of the outer surface of the treatment section; and
a second resin film covering at least a boundary between a region covered by the first resin film and a region not covered by the first resin film on the outer surface of the treatment section,
wherein:
the outer surface includes a treatment surface configured to treat the target of treatment,
the first resin film has an electric resistance and a thermal resistance, at least one of which is higher than that of the treatment section,
the first resin film is located on the outer surface of the treatment section on an opposite side of the treatment surface such that the first resin film does not contact the treatment surface, and
the treatment section bends toward one side in a width direction that intersects with a longitudinal direction and an opening and closing direction and a portion of the second resin film bends along a same curvature as the treatment section.

2. The treatment instrument according to claim 1, wherein the second resin film has a thickness smaller than that of the first resin film, and has at least one of water repellency and oil repellency.

3. The treatment instrument according to claim 1, wherein the treatment section is electrically conductive.

4. The treatment instrument according to claim 1, further comprising a grasping member by which the gap between itself and the treatment section is openable and closable, the grasping member being configured to grasp, by closing the gap between itself and the treatment section, the target of treatment between itself and the treatment section.

5. The treatment instrument according to claim 4, wherein the outer surface of the treatment section includes an opposing surface opposing the grasping member, and
the first resin film is located on the outer surface of the treatment section in a position away from the opposing surface.

6. The treatment instrument according to claim 5, wherein the second resin film covers the opposing surface.

7. The treatment instrument according to claim 1, wherein the treatment section resonates by ultrasonic vibration being transmitted.

8. The treatment instrument according to claim 7, wherein the first resin film includes a distal boundary forming a distal end of the first resin film, the distal boundary being positioned in a distal part of the treatment section, and
the second resin film covers at least a range extending across the distal boundary of the first resin film.

* * * * *